US012136988B2

(12) United States Patent
Liu et al.

(10) Patent No.: US 12,136,988 B2
(45) Date of Patent: Nov. 5, 2024

(54) SIGNAL TRANSMISSION APPARATUS FOR RADIATION EQUIPMENT AND RADIATION SYSTEM (71) Applicant: OUR UNITED CORPORATION, Xi'an (CN)

(72) Inventors: Renqing Liu, Xi'an (CN); Shenfu Liu, Xi'an (CN); Hongbin Zhao, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 324 days.

(21) Appl. No.: 17/681,635

(22) Filed: Feb. 25, 2022

(65) Prior Publication Data
US 2022/0182127 A1 Jun. 9, 2022

Related U.S. Application Data (63) Continuation of application No. PCT/CN2020/094368, filed on Jun. 4, 2020.

(30) Foreign Application Priority Data

Aug. 27, 2019 (CN) .......................... 201910797904.4
Aug. 27, 2019 (CN) .......................... 201921409090.4

(51) Int. Cl.
*A61N 5/10* (2006.01)
*H01Q 1/22* (2006.01)
(Continued)

(52) U.S. Cl.
CPC ............. *H04B 7/15* (2013.01); *A61N 5/1048* (2013.01); *A61N 5/1081* (2013.01); *H01Q 1/22* (2013.01);
(Continued)

(58) Field of Classification Search
None
See application file for complete search history.

(56) References Cited

U.S. PATENT DOCUMENTS 10,594,556 B2 * 3/2020 Washiro .................. H04B 5/72
10,744,346 B2 8/2020 Brodrick
(Continued)

FOREIGN PATENT DOCUMENTS

CN 1915173 A 2/2007
CN 104765072 A 7/2015
(Continued)

OTHER PUBLICATIONS

International search report of PCT application No. PCT/CN2020/094368 issued on Aug. 28, 2020.

*Primary Examiner* — Gary Lafontant
(74) *Attorney, Agent, or Firm* — Knobbe, Martens, Olson & Bear, LLP (57) ABSTRACT

Provided is a signal transmission apparatus for radiation equipment. The signal transmission apparatus includes a first wireless transmission component, the first wireless transmission component includes a first antenna and a second antenna; wherein the first antenna is a loop antenna, and the first antenna is disposed on a gantry in the radiation equipment and is rotatable synchronously with the gantry; and the second antenna is disposed separately from the gantry and is wirelessly connected to the first antenna.

19 Claims, 6 Drawing Sheets (51) Int. Cl.
*H01Q 7/00* (2006.01)
*H01Q 13/20* (2006.01)
*H04B 7/15* (2006.01)

(52) U.S. Cl.
CPC ............ *H01Q 7/00* (2013.01); *H01Q 13/203* (2013.01); *A61N 2005/1074* (2013.01)

(56) References Cited

U.S. PATENT DOCUMENTS

| | | | |
|---|---|---|---|
| 2007/0035883 A1 | 2/2007 | Katcha et al. | |
| 2008/0084345 A1* | 4/2008 | Rougas | H04K 3/42 342/14 |
| 2013/0216018 A1 | 8/2013 | Nakai et al. | |
| 2018/0369613 A1* | 12/2018 | Brodrick | H01Q 3/04 |

FOREIGN PATENT DOCUMENTS

| | | |
|---|---|---|
| CN | 206281573 U | 6/2017 |
| CN | 108168644 A | 6/2018 |
| CN | 109107052 A | 1/2019 |
| CN | 210225406 U | 3/2020 |

\* cited by examiner

SIGNAL TRANSMISSION APPARATUS FOR RADIATION EQUIPMENT AND RADIATION SYSTEM

CROSS-REFERENCE TO RELATED APPLICATION

This application is a continuation application of PCT international patent application No. PCT/CN2020/094368 filed on Jun. 4, 2020, which claims priority to the Chinese Invention Patent Application No. 201910797904.4, filed on Aug. 27, 2019 and entitled "SIGNAL TRANSMISSION APPARATUS FOR RADIATION EQUIPMENT AND RADIATION SYSTEM" and the Chinese Utility Model Patent Application No. 201921409090.4, filed on Aug. 27, 2019 and entitled "SIGNAL TRANSMISSION APPARATUS FOR RADIATION EQUIPMENT AND RADIATION SYSTEM," the disclosures of which are herein incorporated by reference in their entireties.

TECHNICAL FIELD

The present disclosure relates to the field of radiotherapy technologies, and in particular, relates to a signal transmission apparatus for radiation equipment and a radiation system.

BACKGROUND

A radiation system generally includes a host computer, a gantry, and an image acquisition component and a treatment head disposed on the gantry. The gantry may be configured to cause the image acquisition component and the treatment head to rotate.

SUMMARY

The present disclosure provides a signal transmission apparatus for radiation equipment and a radiation system. The technical solutions are as follows.

In a first aspect, a signal transmission apparatus for radiation equipment is provided. The signal transmission apparatus includes a first wireless transmission component, the first wireless transmission component including a first antenna and a second antenna; wherein
  the first antenna is a loop antenna, and the first antenna is disposed on a gantry in the radiation equipment and is rotatable synchronously with the gantry; and
  the second antenna is disposed separately from the gantry and is wirelessly connected to the first antenna.

Optionally, the first wireless transmission component further includes a first wireless bridge and a second wireless bridge; wherein
  the first antenna is connected to the first wireless bridge, the first wireless bridge is configured to be connected to a slave computer, and the first wireless bridge and the slave computer are both disposed on the gantry; and
  the second antenna is connected to the second wireless bridge, the second wireless bridge is configured to be connected to a host computer, and the second wireless bridge and the host computer are both disposed separately from the gantry.

Optionally, the gantry is a ring gantry; and
the first antenna is disposed on an end face of one end of the ring gantry.

Optionally, the first antenna is a loop Radiating Coax Cable.

Optionally, the signal transmission apparatus further includes a second wireless transmission component, the second wireless transmission component including a plurality of third antennas and at least one fourth antenna; wherein
  each of the third antennas is disposed on the gantry and is rotatable synchronously with the gantry; and
  each of the at least one fourth antenna is disposed separately from the gantry and wirelessly connected to each of the third antennas;
wherein a signal transmission bandwidth of the second wireless transmission component is greater than that of the first wireless transmission component.

Optionally, the second wireless transmission component further includes a third wireless bridge and a fourth wireless bridge; wherein
  each of the third antennas is connected to the third wireless bridge, the third wireless bridge is configured to be connected to an image processing component in the radiation equipment, and the third wireless bridge and the image processing component are both disposed on the gantry; and
  each of the at least one fourth antenna is connected to the fourth wireless bridge, the fourth wireless bridge is configured to be connected to a host computer, and the fourth wireless bridge and the host computer are both disposed separately from the gantry.

Optionally, the third antenna is an omnidirectional antenna.

Optionally, an operating frequency band of the third antenna and an operating frequency band of the fourth antenna are both 5 GHz frequency band or 2.4 GHz frequency band.

Optionally, the signal transmission apparatus further includes a wired transmission component; wherein
  the wired transmission component is configured to transmit power signals.

Optionally, the wired transmission component is further configured to transmit data signals and control signals.

Optionally, the wired transmission component includes a slip ring and a carbon brush; wherein
  the slip ring is disposed on the gantry; and
  the carbon brush is disposed separately from the gantry and is in contact with the slip ring.

Optionally, the slip ring and the first antenna are disposed oppositely on two end faces of the gantry.

In a second aspect, a radiation system is provided. The radiation system includes radiation equipment and the signal transmission apparatus as described in the above aspect.

Optionally, the radiation equipment includes a gantry base, and a gantry disposed on the gantry base and rotatably connected to the gantry base; wherein
  the first antenna in the first wireless transmission component in the signal transmission apparatus is disposed on the gantry, and the second antenna in the first wireless transmission component is disposed on the gantry base.

Optionally, the radiation system further includes a slave computer and a host computer; wherein
  the slave computer is disposed on the gantry and is connected to the first wireless bridge in the first wireless transmission component; and
  the host computer is disposed separately from the radiation equipment and is connected to the second wireless bridge in the first wireless transmission component.

BRIEF DESCRIPTION OF THE DRAWINGS

For clearer descriptions of the technical solutions in the embodiments of the present disclosure, the following briefly introduces the accompanying drawings required for describing the embodiments. Apparently, the accompanying drawings in the following description show merely some embodiments of the present disclosure, and those skilled in the art may still derive other drawings from these accompanying drawings without creative efforts.

DETAILED DESCRIPTION

For clearer descriptions of the objectives, technical solutions, and advantages of the present disclosure, embodiments of the present disclosure are described in detail hereinafter with reference to the accompanying drawings.

In the related art, in addition to a host computer, a gantry, and an image acquisition component and a treatment head disposed on the gantry, the radiation system may further include a cable. The host computer and the treatment head as well as the host computer and the image acquisition component may be connected via a cable. Such a cable can be configured for signal transmission.

Figure 1:
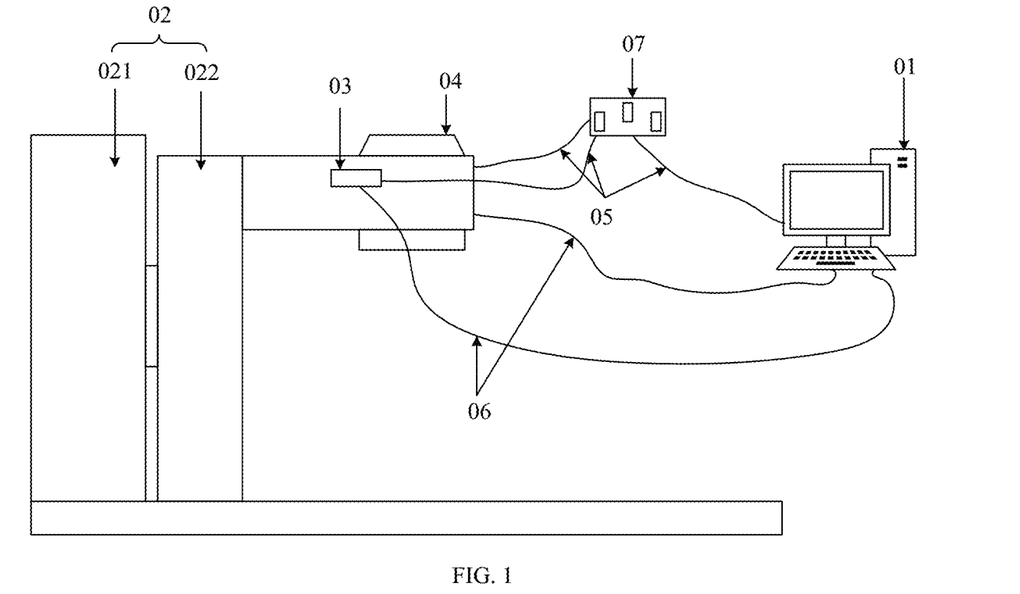
FIG. 1 is a schematic structural diagram of a radiation system in the related art.

FIG. 1 is a schematic structural diagram of a radiation system in the related art. Referring to FIG. 1, the radiation system may include a host computer 01, a gantry 02, an image acquisition component 03 and a treatment head 04 disposed on the gantry 02, a power cable 05, and a signal cable 06. The gantry 02 may include a fixed gantry 021 and a rotating gantry 022. The fixed gantry 021 may be fixedly disposed on the ground. The rotating gantry 022 is rotatably connected to the fixed gantry 021. The image acquisition component 03 and the treatment head 04 may be disposed on the rotating gantry 022. The rotating gantry 022 may drive the image acquisition component 03 and the treatment head 04 to rotate around a rotational axis of the rotating gantry 022.

The host computer 01 may be a control device in the radiation system. The host computer 01 may be configured to control various components in the radiation system. With reference to FIG. 1, the host computer 01 and the image acquisition component 03 as well as the host computer 01 and the treatment head 04 may be both connected via the signal cable 06. The host computer 01 may transmit control signals to the image acquisition component 03 and the treatment head 04 via the signal cable 06. Accordingly, the image acquisition component 03 may also send image information to the host computer 01 via the signal cable 06.

With reference to FIG. 1, the host computer 01, the image acquisition component 03, and the treatment head 04 also need to be connected to a power supply 07 via the power cable 05. The power supply 07 may supply power signals to the host computer 01, the image acquisition component 03, and the treatment head 04, such that the host computer 01, the image acquisition component 03, and the treatment head 04 may be in an operating state.

When the rotating gantry 022 rotates, the image acquisition component 03 and the treatment head 04 disposed on the rotating gantry 022 may rotate accordingly; and both the image acquisition component 03 and the treatment head 04 need to be connected to the power supply 07 via the power cable 05, and connected to the host computer 01 via the signal cable 06, but the length of the power cable 05 and the signal cable 06 is limited; therefore, the rotating gantry 022 can only rotate within an angle range allowed by the length of the power cable 05 and the signal cable 06, which has poor flexibility.

Figure 2:
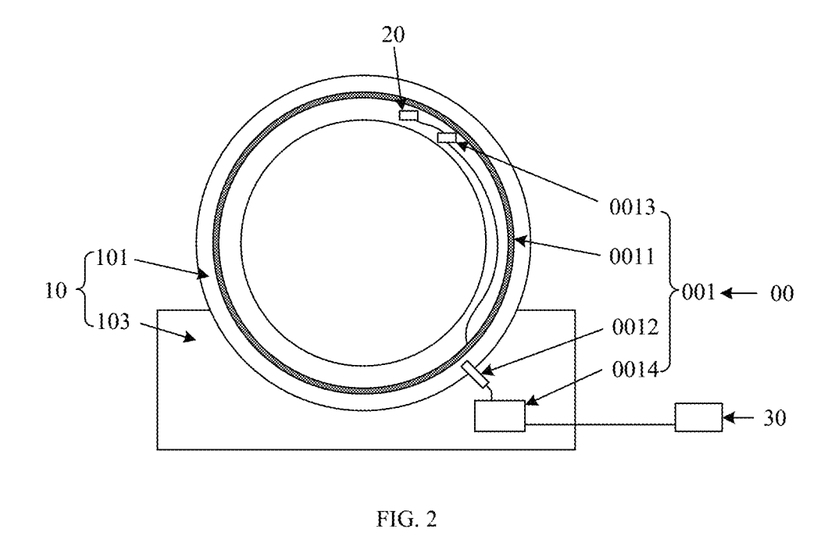
FIG. 2 is a schematic structural diagram of radiation equipment and a signal transmission apparatus according to an embodiment of the present disclosure.

An embodiment of the present disclosure provides a signal transmission apparatus for radiation equipment, which can solve the problem of poor flexibility caused by the fact that the gantry can only rotate within a certain angle range in the related art. With reference to FIG. 2, the signal transmission apparatus 00 may include a first wireless transmission component 001. The first wireless transmission component 001 may include a first antenna 0011 and a second antenna 0012.

The first antenna 0011 may be a loop antenna. The first antenna 0011 may be disposed on the gantry 101 in the radiation equipment 10. The first antenna 0011 is rotatable synchronously with the gantry 101.

The second antenna 0012 may be disposed separately from the gantry 101. The second antenna 0012 may be wirelessly connected to the first antenna 0011.

In the embodiment of the present disclosure, the loop antenna 0011 may be an antenna in a loop shape, and the second antenna 0012 may be an antenna capable of communicating with the loop antenna 0011. For example, the second antenna 0012 may be a cylindrical antenna. The second antenna 0012 may also be referred to as a connecting antenna.

When the gantry 101 rotates, the first antenna 0011 disposed on the gantry 101 may rotate synchronously with the gantry 101, and the second antenna 0012 disposed separately from the gantry 101 remains stationary. That is, when the gantry 101 rotates, the first antenna 0011 disposed on the gantry 101 and the second antenna 0012 disposed separately from the gantry 101 rotate relative to each other. Since the second antenna 0012 is wirelessly connected to the first antenna 0011, that is, the second antenna 0012 and the first antenna 0011 communicate via wireless transmission, the rotation angle of the gantry 101 may not be affected, and the gantry 101 may rotate within any angle range, which has good flexibility.

In summary, an embodiment of the present disclosure provides a signal transmission apparatus for radiation equipment. The signal transmission apparatus may include a first wireless transmission component. The first wireless transmission component includes a first antenna and a second antenna. When a gantry rotates, the first antenna and the second antenna may rotate relative to each other. However, since the first antenna and the second antenna are connected wirelessly, the rotation angle of the gantry may not be affected, and the gantry may rotate within any angle range, which has good flexibility.

Referring to FIG. 2, the first wireless transmission component 001 may further include a first wireless bridge 0013 and a second wireless bridge 0014.

The first antenna 0011 may be connected to the first wireless bridge 0013. The first wireless bridge 0013 may be configured to be connected to a slave computer 20. The first wireless bridge 0013 and the slave computer 20 may both be disposed on the gantry 101. The second antenna 0012 may be connected to the second wireless bridge 0014. The second wireless bridge 0014 may be configured to be connected to a host computer 30. The second wireless bridge 0014 and the host computer 30 may both be disposed separately from the gantry 101.

In the embodiment of the present disclosure, a wireless bridge may be a device that can bridge communication between two or more networks by means of wireless transmission, and such a wireless bridge may also be referred to as a wireless router. The slave computer 20 may be a device that can directly control the radiation equipment 10 and acquire the operating state of the radiation equipment 10. For example, the slave computer 20 may be a programmable logic controller (PLC) or an integrated circuit chip (microcontrollers). The host computer 30 may be a human-machine interaction device capable of directly issuing control commands. For example, the host computer 30 may be a computer. Usually, the host computer 30 receives a control command, and then sends the control command to the slave computer 20; and the slave computer 20 controls the operation of the radiation equipment 10 according to the control command.

Figure 3:
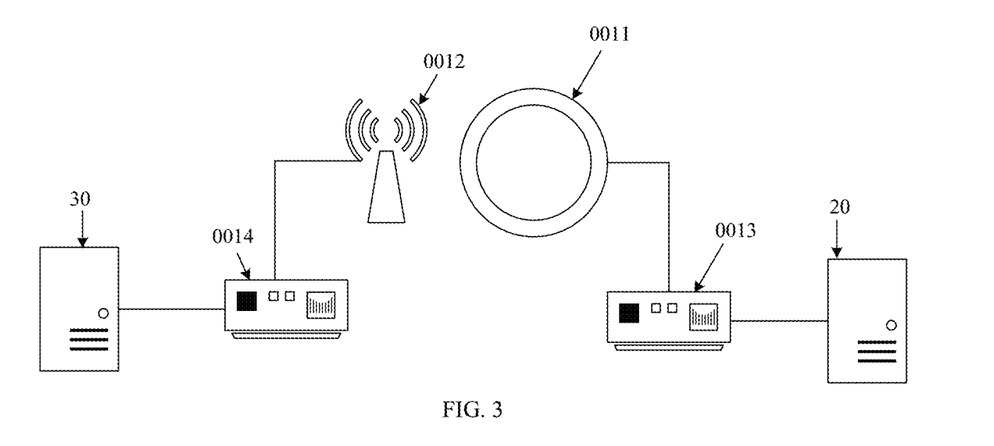
FIG. 3 is a schematic diagram of a first wireless transmission component according to an embodiment of the present disclosure.

FIG. 3 is a schematic diagram of a first wireless transmission component according to an embodiment of the present disclosure. With reference to FIGS. 2 and 3, the first antenna 0011 and the first wireless bridge 0013 as well as the first wireless bridge 0013 and the slave computer 20 may be connected via cables. The second antenna 0012 and the second wireless bridge 0014 as well as the second wireless bridge 0014 and the host computer 30 may be connected via cables.

When the gantry 101 rotates, the first antenna 0011, the first wireless bridge 0013, and the slave computer 20 disposed on the gantry 101 may rotate synchronously. When the gantry 101 remains stationary, the first antenna 0011, the first wireless bridge 0013, and the slave computer 20 disposed on the gantry 101 also remain stationary. That is, no matter whether the gantry 101 rotates or not, the first antenna 0011, the first wireless bridge 0013, and the slave computer 20 are stationary relative to each other. The cables between the first antenna 0011 and the first wireless bridge 0013, and between the first wireless bridge 0013 and the slave computer 20 may not affect the rotation of the gantry 101.

The second antenna 0012, the second wireless bridge 0014, and the host computer 30 are all disposed separately from the gantry 101. Therefore, no matter whether the gantry 101 rotates, the second antenna 0012, the second wireless bridge 0014, and the host computer 30 are stationary relative to each other. The cables between the second antenna 0012 and the second wireless bridge 0014, and between the second wireless bridge 0014 and the host computer 30 may not affect the rotation of the gantry 101.

According to the above analysis, due to the connection via cables that are disposed between the first antenna 0011 and the first wireless bridge 0013, the first wireless bridge 0013 and the slave computer 20, the second antenna 0012 and the second wireless bridge 0014, as well as the second wireless bridge 0014 and the host computer 30 are all stationary relative to each other. Therefore, even if the first antenna 0011 and the second antenna 0012 rotate relative to each other, the rotation angle of the gantry 101 may not be affected, and the gantry 101 may rotate within any angle range, which has good flexibility.

Figure 4:
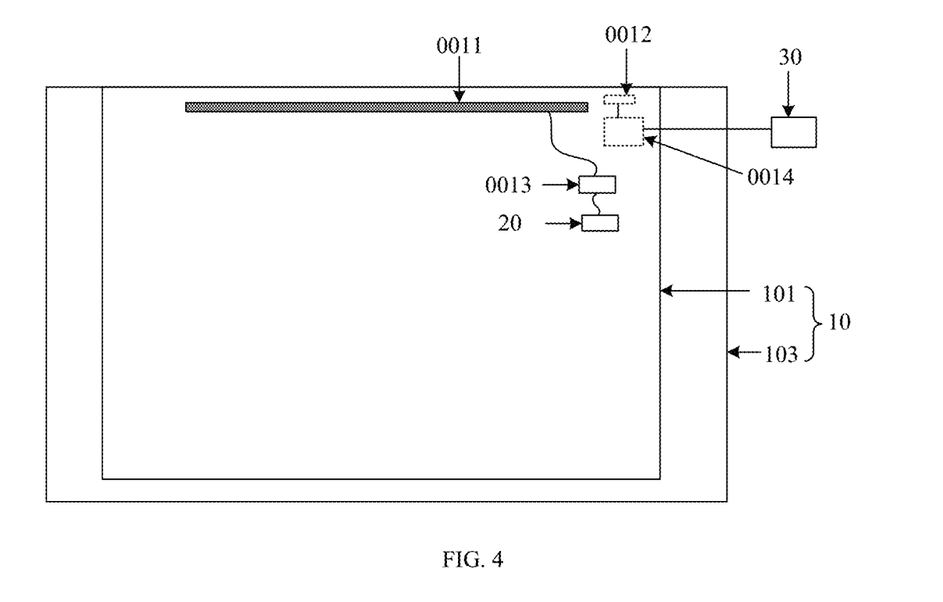
FIG. 4 is a top view of the radiation equipment and signal transmission apparatus shown in FIG. 2.

FIG. 4 is a top view of the radiation equipment and the signal transmission apparatus shown in FIG. 2. As may be seen in combination with FIG. 2 and FIG. 4, the gantry 101 may be a ring gantry. The first antenna 0011 may be disposed on an end face of one end of the ring gantry 101. The first wireless bridge 0013 and the slave computer 20 may both be disposed on a side wall of the ring gantry 101.

The gantry 101 may also be a C-arm gantry or a drum gantry, and the shape of the gantry 101 is not limited in the embodiment of the present disclosure.

Optionally, the first antenna 0011 may be a loop Radiating Coax Cable. The loop Radiating Coax Cable ensures the reliability and stability of data transmission.

Figure 5:
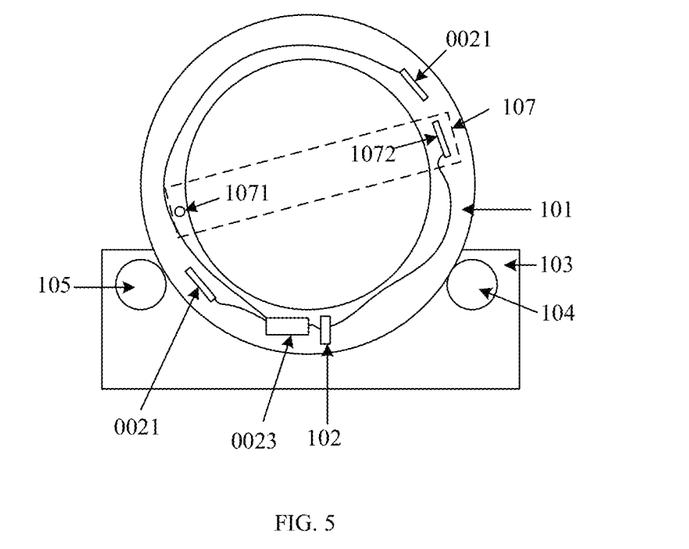
FIG. 5 is a schematic structural diagram of another radiation equipment and signal transmission apparatus according to an embodiment of the present disclosure.
Figure 6:
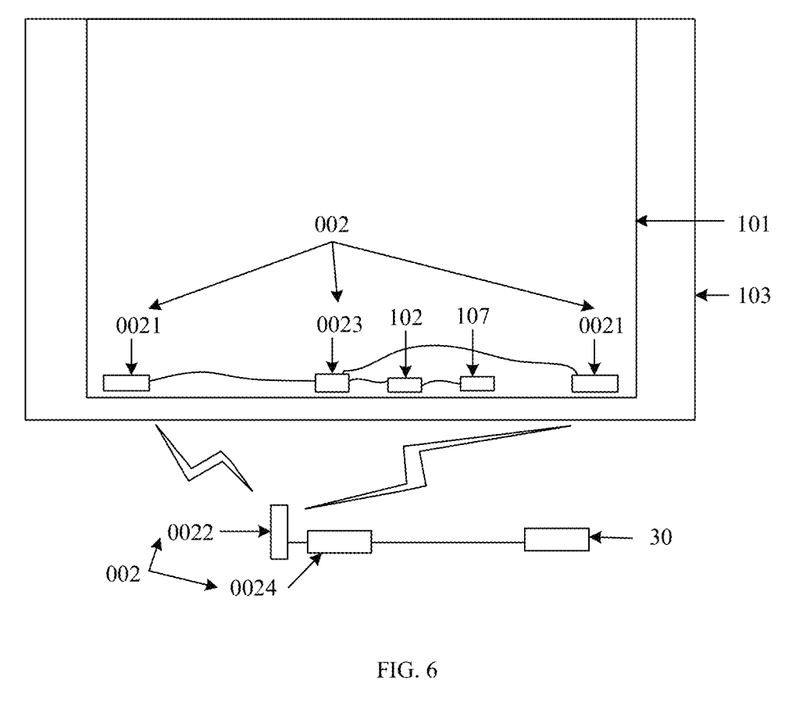
FIG. 6 is a top view of the radiation equipment and signal transmission apparatus shown in FIG. 5.
Figure 7:
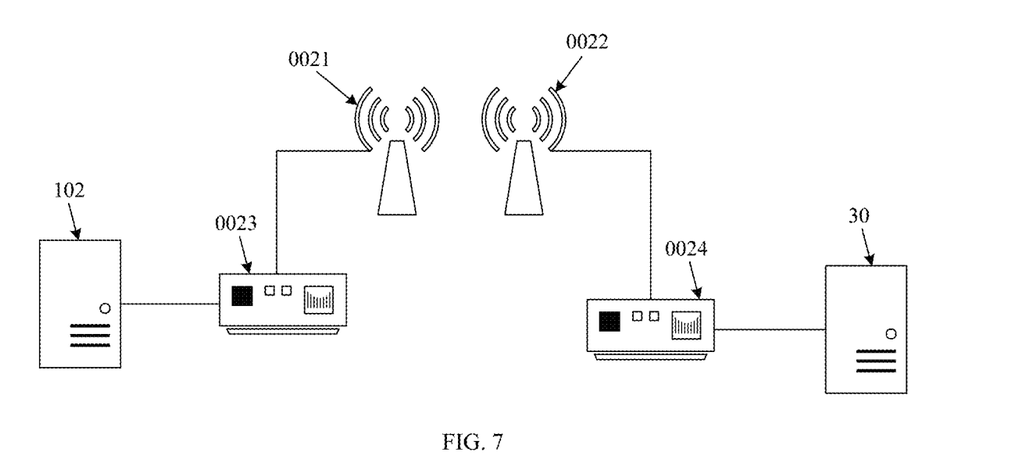
FIG. 7 is a schematic diagram of a second wireless transmission component according to an embodiment of the present disclosure.

FIG. 5 is a schematic structural diagram of another radiation equipment and signal transmission apparatus according to an embodiment of the present disclosure. FIG. 6 is a top view of the radiation equipment and the signal transmission apparatus shown in FIG. 5. FIG. 7 is a schematic diagram of a second wireless transmission component according to an embodiment of the present disclosure. In combination with FIGS. 5 to 7, the signal transmission apparatus 00 may further include a second wireless transmission component 002. The second wireless transmission component 002 may include a plurality of third antennas 0021 and at least one fourth antenna 0022. In an exemplary embodiment, two third antennas 0021 and one fourth antenna 0022 are shown in FIGS. 5 and 6.

Each of the third antennas 0021 may be disposed on the gantry 101 of the radiation equipment 10, and each of the third antennas 0021 is rotatable synchronously with the gantry 101.

Each of the at least one fourth antenna 0022 may be disposed separately from the gantry 101, and the fourth antenna 0022 may be wirelessly connected to each of the third antennas 0021. Optionally, the fourth antenna 0022 may be disposed on a wall of an equipment room where the radiation equipment 10 is placed.

A signal transmission bandwidth of the second wireless transmission component 002 may be greater than that of the first wireless transmission component 001. Therefore, the second wireless transmission component 002 may be configured to transmit signals with larger bandwidth occupancy, and the first wireless transmission component 001 may be configured to transmit signals with smaller bandwidth occupancy.

In the embodiment of the present disclosure, the third antenna 0021 may be an omnidirectional antenna. For example, the third antenna 0021 may have a cylindrical shape, that is, a cylindrical antenna. The fourth antenna 0022 may be a semi-cylindrical antenna, in which a cylindrical surface of the semi-cylindrical antenna is proximal to the third antenna 0021, and a planar surface is disposed distally from the third antenna 0021. The fourth antenna 0022 may also be referred to as a base station antenna.

With reference to FIGS. 5 to 7, the second wireless transmission component 002 may further include a third wireless bridge 0023 and a fourth wireless bridge 0024.

Each of the third antennas 0021 may be connected to the third wireless bridge 0023. The third wireless bridge 0023 may be configured to be connected to the image processing component 102 in the radiation equipment 10. The third wireless bridge 0023 and the image processing component 102 may both be disposed on the gantry 101.

Each of the at least one fourth antenna 0022 may be connected to the fourth wireless bridge 0024. The fourth wireless bridge 0024 may be configured to be connected to the host computer 30. The fourth wireless bridge 0024 and the host computer 30 may both be disposed separately from the gantry 101.

With reference to FIG. 6, the third antenna 0021, the third wireless bridge 0023, and the image processing component 102 may all be disposed on the side wall of the gantry 101. The fourth antenna 0022 and the fourth wireless bridge 0024 may both be disposed on the wall of the equipment room.

It should be noted that the second wireless transmission component 002 is connected to the image processing component 102 and the host computer 30 respectively, and may be configured to transmit image information of the image processing component 102 to the host computer 30.

In the embodiment of the present disclosure, cables may be configured between the third antenna 0021 and the third wireless bridge 0023, the third wireless bridge 0023 and the image processing component 102, the fourth antenna 0022 and the fourth wireless bridge 0024, as well as the fourth wireless bridge 0024 and the host computer 30.

When the gantry 101 rotates, the third antenna 0021, the third wireless bridge 0023, and the image processing component 102 disposed on the gantry 101 may rotate synchronously with the gantry 101, and the third antenna 0021, the third wireless bridge 0023, and the image processing unit 102 are stationary relative to each other. Therefore, the cables between the third antenna 0021 and the third wireless bridge 0023, and between the third wireless bridge 0023 and the image processing unit 102 may not affect the rotation of the gantry 101.

The fourth antenna 0022, the fourth wireless bridge 0024, and the host computer 30 are all disposed separately from the gantry 101. Therefore, no matter whether the gantry 101 rotates, the fourth antenna, the fourth wireless bridge 0024, and the host computer 30 are stationary relative to each other. The cables between the fourth antenna 0022 and the fourth wireless bridge 0024, and between the fourth wireless bridge 0024 and the host computer 30 may not affect the rotation of the gantry 101.

Moreover, since the third antenna 0021 and the fourth antenna 0022 are wirelessly connected, that is, the third antenna 0021 and the fourth antenna 0022 communicate with each other by means of wireless transmission, even when the gantry 101 rotates, the relative rotation between the third antenna 0021 and the fourth antenna 0022 may not affect the rotation of the gantry 101, and the gantry 101 may rotate within any angle range, which has good flexibility.

Optionally, an operating frequency band of the third antenna 0021 and an operating frequency band of the fourth antenna 0022 may be both 5 GHz (gigahertz) frequency band or 2.4 GHz frequency band. The third antenna 0021 and the fourth antenna 0022 have many optional operating frequency bands, which has good application flexibility. The operating frequency bands of the third antenna 0021 and the fourth antenna 0022 are not limited in the embodiment of the present disclosure.

Figure 8:
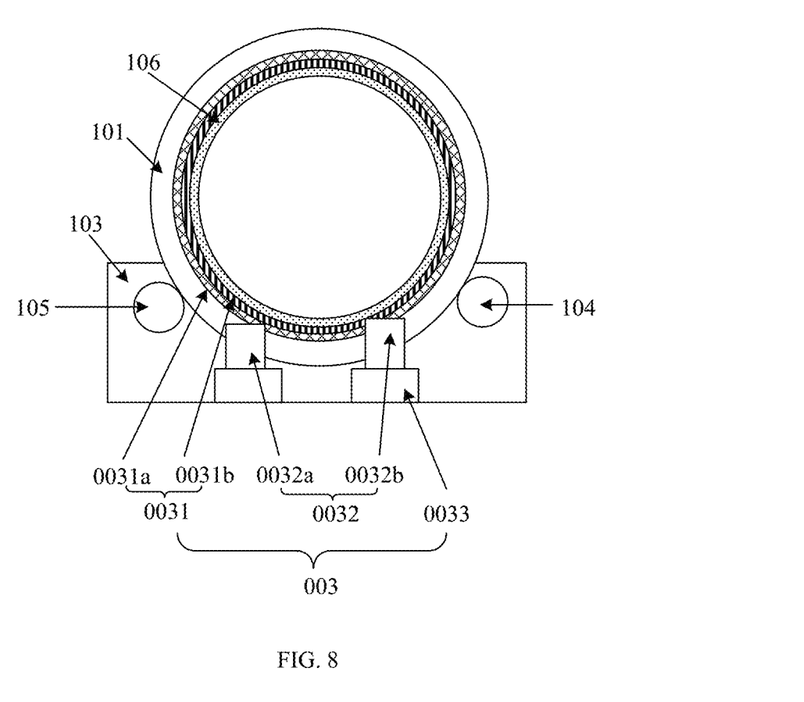
FIG. 8 is a schematic structural diagram of still another radiation equipment and signal transmission apparatus according to an embodiment of the present disclosure.

FIG. 8 is a schematic structural diagram of still another radiation equipment and signal transmission apparatus according to an embodiment of the present disclosure. Referring to FIG. 8, the signal transmission apparatus 00 may further include a wired transmission component 003. The wired transmission component 003 may be configured to transmit power signals. The wired transmission component 003 may also be configured to transmit data signals and control signals.

With reference to FIG. 8, the wired transmission component 003 may include a slip ring 0031 and a carbon brush 0032. The slip ring 0031 may be disposed on the gantry 101. The carbon brush 0032 may be disposed separately from the gantry 101 and may be in contact with the slip ring 0031. The carbon brush 0032 may be configured to be connected to a first control component (not shown in FIG. 8) disposed separately from the gantry 101. The slip ring 0031 may be configured to be connected to a second control component disposed on the gantry 101 (not shown in FIG. 8).

The first control component may be a control cabinet disposed separately from the gantry 101 and integrated with a plurality of components. The second control component may be a control cabinet disposed on the gantry 101. The first control component may be connected to the second control component via the slip ring 0031 and the carbon brush 0032, so as to provide power signals for the second control component. The second control component may also be connected to the slave computer 20, so as to provide power signals for the slave computer 20. Moreover, data signals or control signals may also be transmitted between the first control component and the second control component.

Since the slip ring 0031 and the carbon brush 0032 can maintain contact with each other no matter whether the gantry 101 rotates, the slip ring 0031 and the carbon brush 0032 can realize the signal transmission between the first control component and the second control component. In addition, the connection between the slip ring 0031 and the carbon brush 0032 does not require cables, thus the rotation angle of the gantry 101 may not be affected, and the gantry 101 may rotate within any angle range.

It should be noted that since the slip ring 0031 and the carbon brush 0032 are in direct contact, and the real-time performance of the signal transmission between the first control component and the second control component is good, the slip ring 0031 and the carbon brush 0032 may be configured to transmit signals that require high real-time performance, such as power signals, or transmit at least one of control signals and data signals that require high real-time performance. The control signals may include a gating control signal and an interlock signal.

When the slip ring 0031 and the carbon brush 0032 are adopted to transmit power signals, there is no need to use a power cable to supply power to various components in the radiation equipment 10 with a power cable, thus avoiding the rotation of the gantry 101 being affected by the power cables, and ensuring the rotation flexibility of the gantry 101.

In the embodiment of the present disclosure, the slip ring 0031 may include a plurality of annular conductive tracks. The plurality of conductive tracks may be on an end face of the other end of the gantry 101 along a radial direction of the gantry 101. That is, the slip ring 0031 and the first antenna 0011 may be disposed oppositely on two end faces of the gantry 101.

Optionally, the slip ring 0031 may include a first sub-slip ring 0031*a* and a second sub-slip ring 0031*b*. Each of the sub-slip rings may include a plurality of conductive tracks. The carbon brush 0032 may include a first sub-carbon brush 0032*a* and a second sub-carbon brush 0032*b*. The first sub-slip ring 0031*a* may be in contact with the first sub-carbon brush 0032*a*. The second sub-slip ring 0031*b* may be in contact with the second sub-carbon brush 0032*b*.

The first sub-slip ring 0031*a* and the first sub-carbon brush 0032*a* may be configured to transmit power signals, and the second sub-slip ring 0031*b* and the second sub-carbon brush 0032*b* may be configured to transmit control signals and data signals. The first sub-slip ring 0031*a* and the first sub-carbon brush 0032*a* may also be configured to transmit control signals and data signals, and the second sub-slip ring 0031*b* and the second sub-carbon brush 0032*b* may be configured to transmit power signals, which is not limited in the embodiment of the present disclosure.

In an exemplary embodiment, the slip ring 0031 may include 20 annular conductive tracks, the first sub-slip ring 0031*a* may include nine conductive tracks, and the second sub-slip ring 0031*b* may include 11 conductive tracks. That is, the nine conductive tracks in the first sub-slip ring 0031*a* may be configured to transmit power signals with the first sub-carbon brush 0032*a*. The 11 conductive tracks in the second sub-slip ring 0031*b* may be configured to transmit control signals and data signals with the second sub-carbon brush 0032*b*.

With reference to FIG. 8, the wired transmission component 003 may further include a carbon brush bracket 0033. The carbon brush bracket 0033 may be fixedly connected to the carbon brush 0032. The carbon brush bracket 0033 may be configured to support the carbon brush 0032. With configuration of the carbon brush bracket 0033, it may be ensured that the carbon brush 0032 may not move when the gantry 101 rotates, thereby ensuring the reliability of the signal transmission between the slip ring 0031 and the carbon brush 0032.

In an exemplary embodiment, FIG. 8 shows two carbon brush holders 0033. A certain spacing exists between the two carbon brush holders 0033, such that a spacing is also defined between the first sub-carbon brush 0032*a* and the second carbon brush holder 0032*b* connected respectively to the two carbon brush holders 0033, which is convenient for service technician to routine clean and maintenance.

Figure 9:
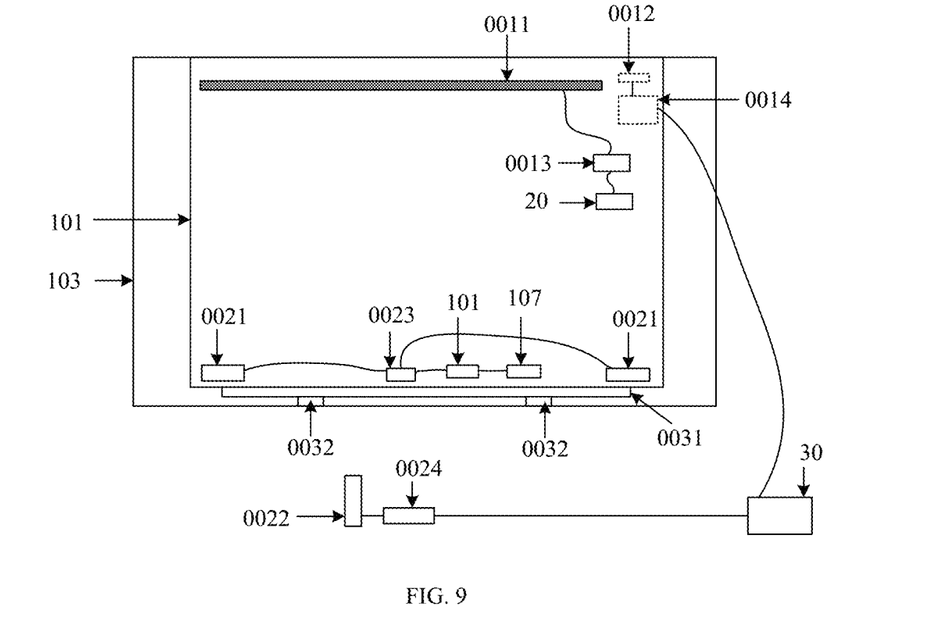
FIG. 9 is a schematic structural diagram of yet another radiation equipment and signal transmission apparatus according to an embodiment of the present disclosure.

FIG. 9 is a schematic structural diagram of yet still another radiation equipment and signal transmission apparatus according to an embodiment of the present disclosure. With reference to FIG. 9, the signal transmission apparatus according to the embodiment of the present disclosure may simultaneously include a first wireless transmission component 001, a second wireless transmission component 002, and a wired transmission component 003.

The first wireless transmission component 001 may be configured to transmit data signals with a small amount of data and small bandwidth occupancy between the slave computer 20 and the host computer 30. The second wireless transmission component 002 may be configured to transmit image signals with a large amount of data and large bandwidth occupancy. The slip ring 0031 and the carbon brush 0032 in the wired transmission component 003 may be configured to transmit at least one of electrical signals, control signals, and data signals that require high real-time performance.

In summary, an embodiment of the present disclosure provides a signal transmission apparatus for radiation equipment. The signal transmission apparatus may include a first wireless transmission component. The first wireless transmission component includes a first antenna and a second antenna. When a gantry rotates, the first antenna and the second antenna may rotate relative to each other. However, since the first antenna and the second antenna are connected wirelessly, the rotation angle of the gantry may not be affected, and the gantry may rotate within any angle range, which has good flexibility.

Figure 10:
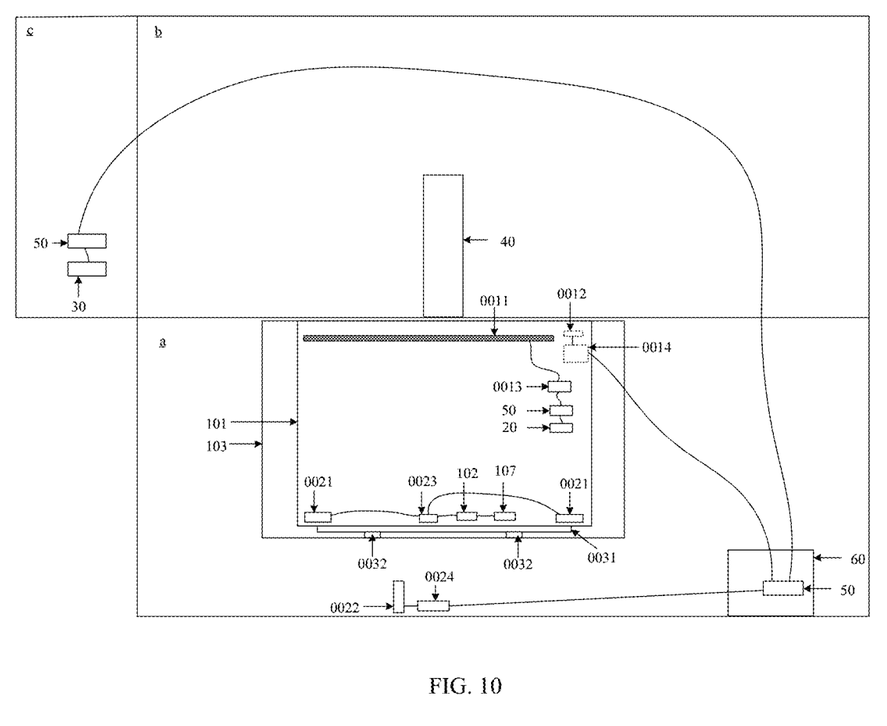
FIG. 10 is a schematic structural diagram of a radiation system according to an embodiment of the present disclosure.

FIG. 10 is a schematic structural diagram of a radiation system according to an embodiment of the present disclosure. With reference to 10, the radiation system may include radiation equipment 10 (the radiation equipment shown in FIG. 10 includes components 101 to 103 and 107) and the signal transmission apparatus 00 according to the above embodiment (the signal transmission apparatus 00 shown in FIG. 10 includes components 0011 to 00134, 0021 to 0024, 0031 and 0032). The signal transmission apparatus may be the signal transmission apparatus 00 shown in any one of FIG. 2, FIG. 4 to FIG. 6, and FIG. 8 to FIG. 9.

In conjunction with FIG. 2, FIGS. 4 to 6, and FIGS. 8 to 10, the radiation equipment 10 may include a gantry base 103, and a gantry 101 disposed on the gantry base 103 and rotatably connected to the gantry base 103. The gantry 101 may rotate around a rotational axis of the gantry 101.

In the embodiment of the present disclosure, the first antenna 0011 in the first wireless transmission component 001 of the signal transmission apparatus 00 may be disposed on the gantry 101. The second antenna 0012 and the second wireless bridge 0014 may both be disposed on the gantry base 103. The host computer 30 may be disposed separately from the gantry 101 and the gantry base 103. Since the gantry base 103 may be disposed on the ground or on a load-bearing surface, the second antenna 0012 and the second wireless bridge 0014 disposed on the gantry base 103 and the host computer 30 disposed separately from the gantry 101 and the gantry base 103 may remain stationary, no matter whether the gantry 101 rotates. The cables between the second antenna 0012 and the second wireless bridge 0014, and between the second wireless bridge 0014 and the host computer may not affect the rotation of the gantry 101.

Since the first antenna 0011 is disposed on the gantry 101, and the second antenna 0012 is disposed on the gantry base 103, the pitch between the first antenna 0011 and the second antenna 0012 may be relatively small, thereby improving the reliability and stability of data transmission between the first antenna 0011 and the second antenna 0012.

Optionally, the pitch ranges between the first antenna 0011 and the second antenna 0012 may be from 30 mm (millimeters) to 40 mm. The pitch may refer to the shortest distance between the first antenna 0011 and the second antenna 0012.

With reference to FIG. 5 and FIG. 8, the radiation equipment 10 may further include a driving wheel 104 and a driven wheel 105. The driving wheel 104 and the driven wheel 105 may both be fixedly connected to the gantry base 103, may be disposed respectively on two sides of the gantry 101, and may both be in contact with the gantry 101. The driving wheel 104 may be connected to a driving component (not shown in FIGS. 5 and 8). The driving component may be configured to drive the driving wheel 104 to rotate, and driving wheel 104 may in turn drive the gantry 101 to rotate. When the gantry 101 rotates, the driven wheel 105 rotates accordingly. The driving wheel 104 and the driven wheel 105 may provide support to the gantry 101 to ensure the stability of the rotation of the gantry 101. The driving component may be a drive motor.

Optionally, the radiation equipment 10 may further include a centering ring 106. The centering ring 106 may be disposed on the gantry 101. The centering ring 106 may be fixedly connected to both the gantry 101 and the slip ring 0031. An axis of the centering ring 106, an axis of the slip ring 0031, and a rotational axis of the gantry 101 may be collinear. Moreover, a diameter of the centering ring 106 may be less than that of the slip ring 0031.

In the process of installing the radiation equipment 10, the centering ring 106 may be first connected to the gantry 101, while it is ensured that the axis of the centering ring 106 and the rotational axis of the gantry 101 are collinear. After that, the slip ring 0031 may be connected to the centering ring 106. For example, the slip ring 0031 may be sleeved on the centering ring 106, so as to ensure that the axis of the slip ring 0031 and the axis of the centering ring 106 are collinear.

According to the above analysis, with configuration of the centering ring 106, the axis of the slip ring 0031 may be collinear with the rotational axis of the gantry 101, and the slip ring 0031 may be prevented from jumping during the rotation of the gantry 101 as well, so as to ensure the reliability of signal transmission between the slip ring 0031 and the carbon brush 0032.

The radiation equipment 10 may not be necessarily provided with the centering ring 106. The gantry 101 may be provided with a first connecting hole. The slip ring 0031 may be provided with a second connecting hole corresponding to the first connecting hole. Bolts can fix the slip ring 0031 by passing through the first connecting hole and the second connecting hole. Thus, it may be ensured that the axis of the slip ring 0031 is collinear with the rotational axis of the gantry 101, preventing the slip ring 0031 from jumping during the rotation of the gantry 101, and ensuring the reliability of the signal transmission between the slip ring 0031 and the carbon brush 0032.

In the embodiment of the present disclosure, with reference to FIG. 5, the radiation equipment 10 may further include an image processing component 102 and an image acquisition component 107 disposed on the gantry 101. The image acquisition component 107 may be connected to the image processing component 102. The image acquisition component 107 may transmit image information as acquired to the image processing component 102. The image processing component 102 transmits the image information to the host computer 30 via the second wireless transmission component 002.

The image acquisition component 107 may be cone beam computed tomography (CBCT). The CBCT may also be referred to as a flat panel imaging system. The image acquisition component 107 may include a bulb 1071 and a detector 0172. The second wireless transmission component 002 according to the embodiment of the present disclosure may be configured to transmit image information with a large amount of data and large bandwidth occupancy.

In the embodiment of the present disclosure, FIG. 5 shows only one bulb 1071 and one detector 0172. The image acquisition component 107 may include a plurality of bulbs 1071 and a plurality of detectors 0172, which is not limited in the embodiment of the present disclosure.

Referring to FIG. 10, the radiation system may further include a slave computer 20 and a host computer 30. The slave computer 20 may be disposed on the gantry 101. The slave computer 20 may be connected to the first wireless bridge 0012 in the first wireless transmission component 001. The host computer 30 may be disposed separately from the radiation equipment 10. The host computer 30 may be connected to the second wireless bridge 0014 in the first wireless transmission component 001.

In the embodiment of the present disclosure, the radiation system may further include a patient support apparatus 40. The patient support apparatus 40 may be a bed or a chair for supporting a patient, such as a treatment couch, a diagnostic couch, a treatment seat, a diagnostic seat, and the like.

Referring to FIG. 10, the radiation equipment 10 may be disposed in an equipment room a, the patient support apparatus 40 may be disposed in a treatment room b, and the host computer 30 may be disposed in a control room c. The radiation equipment 10 is controlled by the host computer 30 in the control room c to treat the patient in the treatment room b.

With the radiation equipment 10 being disposed in the equipment room a and the host computer 30 being disposed in the control room c, the radiation equipment 10 is prevented from causing to the body of the treating physician during treatment. In addition, a block (or may be called a skin) may be disposed between the equipment room a and the treatment room b, such that the radiation equipment is invisible to the patient, and the appearance is better.

With reference to FIG. 10, the radiation system may further include a switch 50. The switch 50 may be connected to various wireless bridges in the radiation equipment. The switch 50 may also be connected to the slave computer 20 and the host computer 30, respectively. That is, the wireless bridges may be connected to the slave computer 20 or the host computer 30 via the switch 50.

Optionally, the switch 50 for connecting the slave computer 20 may be disposed on the side wall of the gantry 101 in the radiation equipment 10. The switch 50 for connecting the host computer 30 may be disposed in the control room c.

The radiation system may further include a first control component 60 and a second control component (not shown in FIG. 10). The first control component 60 may be disposed in the equipment room a, and a switch 50 may also be disposed in the first control component 60. The first control component 60 and the second control component may both be referred to as control cabinets.

With reference to FIG. 10, the first wireless transmission component 001 may be located on an end face of an end of the gantry 101 proximal to the treatment room b. The second wireless transmission component 002 may be disposed at one end of the gantry 101 away from the treatment room b. The wired transmission component 003 may be disposed on an end face of an end of the gantry 101 distal from the treatment room b. The third antenna 0021 and the third wireless bridge 0023 in the second wireless transmission component 002 may be disposed on the side wall of an end of the gantry 101 distal from the treatment room b. The fourth antenna 0022 and the fourth wireless bridge 0024 may be disposed on the wall of the gantry 101 distal from the treatment room b.

It should be noted that, the radiation system according to the embodiment of the present disclosure may be a radiation therapy system, and the radiation equipment may be radiation therapy equipment.

In summary, an embodiment of the present disclosure provides a radiation system. The system may include radiation equipment and the signal transmission apparatus according to the above embodiment. When the gantry in the radiation equipment rotates, the first antenna and the second antenna in the signal transmission apparatus may rotate relative to each other. However, since the first antenna and the second antenna are connected wirelessly, the rotation angle of the gantry may not be affected, and the gantry may rotate within any angle range, which has better flexibility.

Described above are merely exemplary embodiments of the present disclosure, and are not intended to limit the present disclosure. Within the spirit and principles of the disclosure, any modifications, equivalent substitutions, improvements, and the like are within the protection scope of the present disclosure.

What is claimed is:

1. A signal transmission apparatus for radiation equipment, comprising:
a first wireless transmission component, the first wireless transmission component comprising a first antenna and a second antenna, wherein:
the first antenna is a loop antenna, and the first antenna is disposed on a gantry in the radiation equipment and is rotatable synchronously with the gantry; and
the second antenna is disposed separately from the gantry and is wirelessly connected to the first antenna; and
a second wireless transmission component, the second wireless transmission component comprising a plurality of third antennas and at least one fourth antenna, wherein:
each of the plurality of third antennas is disposed on the gantry and is rotatable synchronously with the gantry; and
each of the at least one fourth antenna is disposed separately from the gantry and is wirelessly connected to each of the plurality of third antennas,
wherein a signal transmission bandwidth of the second wireless transmission component is greater than that of the first wireless transmission component.

2. The signal transmission apparatus according to claim 1, wherein the first wireless transmission component further comprises a first wireless bridge and a second wireless bridge, and wherein:
the first antenna is connected to the first wireless bridge, the first wireless bridge is configured to be connected to a slave computer, and the first wireless bridge and the slave computer are both disposed on the gantry; and
the second antenna is connected to the second wireless bridge, the second wireless bridge is configured to be connected to a host computer, and the second wireless bridge and the host computer are both disposed separately from the gantry.

3. The signal transmission apparatus according to claim 2, wherein;
the first antenna is connected to the first wireless bridge via a cable, and the first wireless bridge is connected to the slave computer via a cable; and
the second antenna is connected to the second wireless bridge via a cable, and the second wireless bridge is connected to the host computer via a cable.

4. The signal transmission apparatus according to claim 1, wherein:
the gantry is a ring gantry; and
the first antenna is disposed on an end face of one end of the ring gantry.

5. The signal transmission apparatus according to claim 1, wherein the first antenna is a loop Radiating Coax Cable.

6. The signal transmission apparatus according to claim 1, wherein the second wireless transmission component further comprises a third wireless bridge and a fourth wireless bridge, and wherein;
each of the plurality of third antennas is connected to the third wireless bridge, the third wireless bridge is configured to be connected to an image processing component in the radiation equipment, and the third wireless bridge and the image processing component are both disposed on the gantry; and
each of the at least one fourth antenna is connected to the fourth wireless bridge, the fourth wireless bridge is configured to be connected to a host computer, and the fourth wireless bridge and the host computer are both disposed separately from the gantry.

7. The signal transmission apparatus according to claim 6, wherein:
each of the plurality of third antennas is connected to the third wireless bridge via a cable, and the third wireless bridge is connected to the image processing component via a cable; and
each of the at least one fourth antenna is connected to the fourth wireless bridge via a cable, and the fourth wireless bridge is connected to the host computer via a cable.

8. The signal transmission apparatus according to claim 1, wherein a third antenna of the plurality of third antennas is an omnidirectional antenna.

9. The signal transmission apparatus according to claim 1, wherein an operating frequency band of a third antenna of the plurality of third antennas and an operating frequency band of the at least one fourth antenna are both 5 GHz frequency band or 2.4 GHz frequency band.

10. The signal transmission apparatus according to claim 1, further comprising a wired transmission component,
wherein the wired transmission component is configured to transmit power signals.

11. The signal transmission apparatus according to claim 10, wherein the wired transmission component is further configured to transmit data signals and control signals.

12. The signal transmission apparatus according to claim 10, wherein the wired transmission component comprises a slip ring and a carbon brush, wherein;
the slip ring is disposed on the gantry; and
the carbon brush is disposed separately from the gantry and is in contact with the slip ring.

13. The signal transmission apparatus according to claim 12, wherein the slip ring and the first antenna are disposed oppositely on two end faces of the gantry.

14. The signal transmission apparatus according to claim 12, wherein the slip ring comprises a first sub-slip ring and a second sub-slip ring, wherein the carbon brush comprises a first sub-carbon brush and a second sub-carbon brush and wherein:
the first sub-slip ring is in contact with the first sub-carbon brush, and the second sub-slip ring is in contact with the second sub-carbon brush; and
the first sub-slip ring and the first sub-carbon brush are configured to transmit power signals, and the second sub-slip ring and the second sub-carbon brush are configured to transmit control signals and data signals.

15. The signal transmission apparatus according to claim 12, wherein the carbon brush is configured to be connected to a first control component disposed separately from the gantry, the slip ring is configured to be connected to a second control component disposed on the gantry, and the second control component is also connected to a slave computer.

16. A radiation system, comprising:
a radiation equipment and a signal transmission apparatus for the radiation equipment,
wherein the signal transmission apparatus for the radiation equipment comprises a first wireless transmission component, the first wireless transmission component comprising a first antenna and a second antenna;
wherein;

the first antenna is a loop antenna, and the first antenna is disposed on a gantry in the radiation equipment and is rotatable synchronously with the gantry; and the second antenna is disposed separately from the gantry and is wirelessly connected to the first antenna;

wherein the signal transmission apparatus for radiation equipment further comprises a second wireless transmission component, the second wireless transmission component comprising a plurality of third antennas and at least one fourth antenna;

wherein:

each of the plurality of third antennas is disposed on the gantry and is rotatable synchronously with the gantry; and each of the at least one fourth antenna is disposed separately from the gantry and is wirelessly connected to each of the plurality of third antennas; and wherein a signal transmission bandwidth of the second wireless transmission component is greater than that of the first wireless transmission component.

17. The radiation system according to claim 16, wherein the radiation equipment comprises a gantry base, and a gantry disposed on the gantry base and rotatably connected to the gantry base; and wherein the first antenna in the first wireless transmission component in the signal transmission apparatus is disposed on the gantry, and the second antenna in the first wireless transmission component is disposed on the gantry base.

18. The radiation system according to claim 17, further comprising a slave computer and a host computer, and wherein the first wireless transmission component further comprises a first wireless bridge and a second wireless bridge;

wherein:

the slave computer is disposed on the gantry and is connected to the first wireless bridge in the first wireless transmission component; and the host computer is disposed separately from the radiation equipment and is connected to the second wireless bridge in the first wireless transmission component.

19. The radiation system according to claim 18, wherein the host computer is further connected to a second wireless transmission component in the signal transmission apparatus; and the radiation equipment further comprises an image processing component and an image acquisition component disposed on the gantry; and wherein:

the image acquisition component is connected to the image processing component and is configured to transmit image information as acquired to the image processing component; and the image processing component is also connected to the second wireless transmission component and is configured to transmit the image information to the host computer via the second wireless transmission component.

* * * * *